(12) United States Patent
Wittrig et al.

(10) Patent No.: US 11,821,868 B2
(45) Date of Patent: Nov. 21, 2023

(54) DETECTION AND ANALYSIS OF OLEFINS IN PETROLEUM BY ELECTROSPRAY IONIZATION MASS SPECTROMETRY

(71) Applicant: ExxonMobil Technology and Engineering Company, Annandale, NJ (US)

(72) Inventors: Ashley M. Wittrig, Houston, TX (US); Kuangnan Qian, Skillman, NJ (US); Thomas R. Fredriksen, Milford, NJ (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 453 days.

(21) Appl. No.: 17/205,528

(22) Filed: Mar. 18, 2021

(65) Prior Publication Data

US 2021/0302371 A1   Sep. 30, 2021

Related U.S. Application Data

(60) Provisional application No. 63/001,597, filed on Mar. 30, 2020.

(51) Int. Cl.
*G01N 27/626* (2021.01)
*H01J 49/16* (2006.01)
*G01N 1/38* (2006.01)
*H01J 49/38* (2006.01)

(52) U.S. Cl.
CPC .............. *G01N 27/628* (2013.01); *G01N 1/38* (2013.01); *H01J 49/165* (2013.01); *H01J 49/38* (2013.01)

(58) Field of Classification Search
CPC ........ G01N 27/628; G01N 1/38; G01N 27/62; G01N 33/2823; H01J 49/165; H01J 49/38
See application file for complete search history.

(56) References Cited

U.S. PATENT DOCUMENTS

| | | | |
|---|---|---|---|
| 7,985,718 B2 * | 7/2011 | Steinbrenner | C09K 8/584 507/252 |
| 2011/0253152 A1 * | 10/2011 | Lin | D04H 1/4291 128/849 |
| 2015/0038750 A1 * | 2/2015 | Weiss | C25B 1/26 422/186 |
| 2018/0312771 A1 * | 11/2018 | Abdallah | C10G 45/00 |

(Continued)

OTHER PUBLICATIONS

Sokol, W.; et. al. Am. Chem. Soc., Div. Fuel Chem. 2010, 55, 180.

(Continued)

*Primary Examiner* — Christopher P Mcandrew
*Assistant Examiner* — Zannatul Ferdous
(74) *Attorney, Agent, or Firm* — Vorys, Sater, Seymour, and Pease LLP

(57) ABSTRACT

A method for detecting and analyzing olefins in petroleum by electrospray ionization mass spectrometry can include obtaining a hydrocarbon sample comprising at least about 90 wt % of saturate compounds; producing a solution comprising the hydrocarbon sample and a metal salt, the metal salt comprising a metal ion; forming olefin-metal ion complexes by electrospray ionization; and detecting the olefin-metal ion complexes using mass spectrometry.

20 Claims, 4 Drawing Sheets

(56) References Cited

U.S. PATENT DOCUMENTS

2019/0010381 A1\* 1/2019 Nguyen ................. C09K 8/584
2020/0115809 A1\* 4/2020 Leclerc .................... C25B 9/19

OTHER PUBLICATIONS

Jackson, A.; et. al. Anal. Bioanal. Chem. 2011, 399, 367-376.
Ng, K. M; et. al. Rapid Commun. Mass Spectrom. 1999, 12, 1679-1684.
Nazari, M.; et. al. Anal. Bioanal. Chem. 2018, 410, 953-962.
Meier, F.; et. al. Rapid Commun. Mass Spectrom. 2014, 28, 2461-247.

\* cited by examiner

DETECTION AND ANALYSIS OF OLEFINS IN PETROLEUM BY ELECTROSPRAY IONIZATION MASS SPECTROMETRY

CROSS-REFERENCE TO RELATED APPLICATION

This application relates and claims priority to U.S. Ser. No. 63/001,597, filed on Mar. 30, 2020, the disclosure of which is incorporated herein by reference in its entirety.

FIELD OF THE INVENTION

This application relates to methods for detecting and analyzing olefins in petroleum by electrospray ionization mass spectrometry.

BACKGROUND

Petroleum samples are complicated hydrocarbon mixtures containing paraffins, cyclic paraffins (naphthenes), multi-ring aromatics, and various heteroatomic hydrocarbons (most commonly with O, S, and N heteroatoms). In addition, petroleum samples may contain trace amount of olefins. These olefins are generally produced during thermal and/or catalytic cracking processes. Olefins can easily be oxidized and can cause instability in hydrocarbon intermediate streams and products. In particular, trace levels of olefins in lubricant oil base stocks can cause serious quality problems. As such, detection and analysis of olefins in petroleum compositions can improve the operation of subsequent processes.

Detection and compositional analysis of low levels of olefins in high boiling complex mixtures such as base stocks and bright stocks (high-viscosity, paraffinic base oils produced from vacuum resid by means of solvent extraction of asphaltenes, wax, and aromatics) is a current analytical challenge. Gas chromatography technology, such as PIONA (paraffins, isoparaffins, olefins, naphthenes, aromatics) analysis, can detect and quantify olefins in the gasoline and naphtha range. Supercritical fluid chromatography (SFC) can quantify olefins in diesel and light gas oils. A combination of SFC-FIMS (field ionization mass spectrometry) is currently used to determine the molecular composition of olefins in diesel boiling range materials. As boiling point increases, however, separation of olefins from naphthenes becomes difficult, especially if olefins are present at trace levels. In mass spectrometry, analysis using traditional ionization methods, such as field ionization, cannot distinguish between isomeric olefins and cyclic paraffins because of their identical elemental formulas. While nuclear magnetic resonance (NMR) spectroscopy may be able to detect their presence, the molecular composition is obscured. Additionally, NMR is limited to olefinic carbon having concentrations above a certain level such that trace levels of olefins cannot be detected with via NMR.

Accordingly, there is a need for the analysis and detection of olefins from high boiling complex mixtures such as lubricant base stocks and bright stocks.

SUMMARY

This application relates to methods for detecting and analyzing olefins in petroleum by electrospray ionization mass spectrometry.

Methods described herein may comprise obtaining a hydrocarbon sample comprising at least about 90 wt % of saturate compounds; producing a solution comprising the hydrocarbon sample and a metal salt, the metal salt comprising a metal ion; forming olefin-metal ion complexes by electrospray ionization; and detecting the olefin-metal ion complexes using mass spectrometry.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one of ordinary skill in the art and having the benefit of this disclosure.

DETAILED DESCRIPTION

Figure 1A:
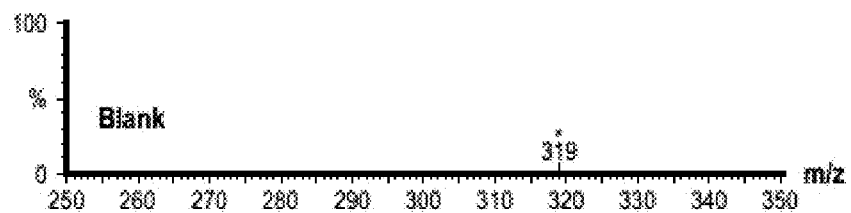
FIGS. 1A-1D show the mass spectra of an instrument blank (A), of olefin 1-hexadecene (B), of non-olefinic cyclohexylhexane (C), and of mixture of 1-hexadecene and cyclohexylhexane (D) obtained in Example 1.
Figure 1B:
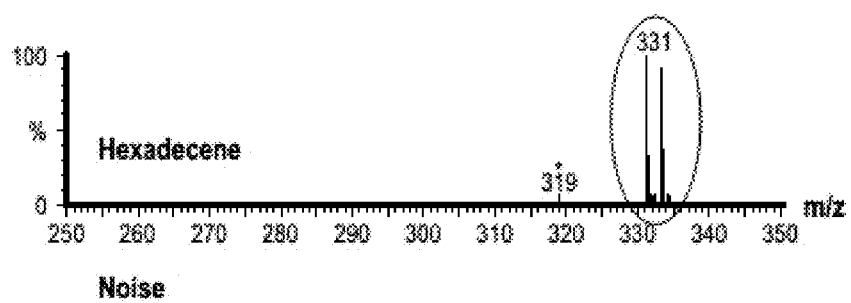
Figure 1C:
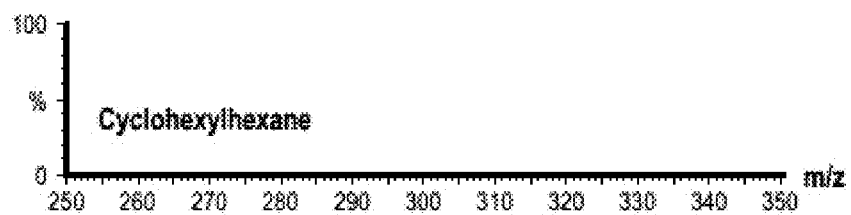

The present application relates to methods for the selective detection and compositional analysis of olefins in high boiling petroleum fractions, such as lubricant base stock and bright stock. According to the methods described herein, olefins may be detected among mixtures of saturated hydrocarbon molecules without prior separation from the bulk solutions containing the mixtures. More particularly, the methods described herein allow for low level olefin detection and compositional determination in mixtures such as hydrotreated petroleum product, petroleum base stocks etc.

These methods require minimal sample preparation prior to analysis. In these methods, the sample is dissolved in solution with an additive. This is in contrast with methods requiring a sample preparation carried out in multiple stages including the physical separation of olefins, which may be very difficult depending on the nature of the sample or extremely challenging for samples in which the olefin concentration is low. For example, some methods use a solid sample, in which molecules are desorbed from the surface followed by selective ionization of the olefins, the analysis thus missing the bulk composition. Other methods use high boiling liquids and include the sample preparation step of depositing the liquid on a solid surface. As such, the methods of the present application are applicable to a broader range of sample types, allow for analysis of the bulk sample, and involve a much simpler sample preparation.

The methods described herein may use metal ion assisted electrospray ionization to selectively ionize olefins among other non-olefinic molecules in a complex mixture without prior separation from the mixture. In these methods, the test sample may be prepared by dissolving a sample of the liquid to be analyzed in a non-aromatic, non-olefinic solvent or a mixture of non-aromatic, non-olefinic solvents based on the sample solubility and adding an ionization reagent dissolved in a solvent that can both solubilize the ionization reagent and at least be miscible in the sample solvent at the concentration used. The metal ions preferentially form complexes with the π electrons in the double bonds of the olefins upon electrospraying, thus adding a charge only to those molecules. Since mass spectrometry analysis detects only charged species, olefins are the only species observed on detection.

In addition, Fourier-transform ion cyclotron resonance mass spectrometry (FT-ICR MS) or other forms of high resolution mass spectrometry may be used for the olefin analysis in the methods described herein. FT-ICR MS allows for ultra-high mass resolution and determination of masses with high accuracy (error <0.2 ppm). In FT-ICR MS, the excited cyclotron motion of the ions is detected on receiver plates as a time domain signal that contains all the cyclotron frequencies that have been excited. Fourier transformation of the time domain signal results in the frequency domain signal that can be converted into a mass spectrum. FT-ICR MS may provide compositional information including the classes of compounds (e.g., aromatics, olefins), the Z-number distribution (or homologous series distribution) within each compound class (Z being defined as hydrogen deficiency as in general chemical formula, $C_cH_{2c+z}$, so that the more negative the Z-number, the more unsaturated the molecules), and the total carbon number distribution or molecular weight distribution of each homolog.

Double bond equivalents (DBE) is another representation of hydrogen deficiency where each ring and double bond equates to 1 DBE. The DBE of a molecule can be calculated from a chemical formulae according to Eq. 1:

$$DBE = C - \frac{H}{2} + \frac{N}{2} + 1 \qquad \text{Eq. 1}$$

Where C, H, N are number of carbon, hydrogen and nitrogen atoms in a molecule, respectively. Eq. 2 can be used to convert between Z number and DBE.

$$DBE = \frac{-1}{2}(Z) + 1 \qquad \text{Eq. 2}$$

The methods described herein are suitable for detection and analysis of a hydrocarbon samples that may contain heavy hydrocarbons such as from the petroleum saturates portion of a petroleum feed. A hydrocarbon sample can be a sample from one or more feedstocks, products, and/or intermediate feeds or products that correspond to a heavy hydrocarbon fraction. Unless otherwise specified, a "hydrocarbon" fraction, sample, feedstock, or product is defined herein to include fractions, samples, feedstocks, or products that include carbon and hydrogen atoms. Unless otherwise specified, a reference to a hydrocarbon sample represents a portion of a hydrocarbon fraction, feedstock, product, or other hydrocarbon source that is used in order to characterize the properties of the hydrocarbon source.

As used herein, and unless otherwise specified, the terms "olefin" and "olefinic hydrocarbon," alternatively referred to as "alkene," refer to one or more unsaturated hydrocarbon compound containing at least one carbon atom directly bound to another carbon atom by a double bond. In other words, an olefin is a compound which contains at least one pair of carbon atoms, where the first and second carbon atoms of the pair are directly linked by a double bond. An olefin may be straight chain or branched chain, or contain naphthene rings. Non-limiting examples include ethylene, propylene, butylene, and pentene. "Olefin" is intended to embrace all structural isomeric forms of olefins.

As used herein, and unless otherwise specified, the terms "aromatics" and "aromatic hydrocarbon" mean unsaturated cyclic hydrocarbons having a delocalized conjugated π system and having from six to sixty carbon atoms (e.g., aromatic $C_6$-$C_{60}$ hydrocarbon). Examples of suitable aromatics include, but are not limited to benzene, toluene, xylenes, mesitylene, ethylbenzenes, cumene, naphthalene, methylnaphthalene, dimethylnaphthalenes, ethylnaphthalenes, acenaphthalene, anthracene, phenanthrene, tetraphene, naphthacene, benzanthracenes, fluoranthrene, pyrene, chrysene, triphenylene, and the like, and combinations thereof. Additionally, an aromatic may comprise one or more heteroatoms. Examples of heteroatoms include, but are not limited to, nitrogen, oxygen, and/or sulfur. Aromatics with one or more heteroatom include, but are not limited to thiophene, benzothiophene, oxazole, thiazole and the like, and combinations thereof. An aromatic may comprise monocyclic, bicyclic, tricyclic, and/or polycyclic rings (in any embodiment, at least monocyclic rings, only monocyclic and bicyclic rings, or only monocyclic rings) and may be fused rings. As used herein, the plural use of "xylenes" and grammatical variations thereof is used to convey that the xylene may be any isomer of xylene, including m-xylene, o-xylene, p-xylene, or any blend thereof.

As used herein, and unless otherwise specified, the term "paraffin," alternatively referred to as "alkane," and grammatical derivatives thereof, refers to a saturated hydrocarbon chain of one to about one hundred carbon atoms in length, such as, but not limited to methane, ethane, propane and butane. A paraffin may be straight-chain, cyclic or branched-chain. "Paraffin" is intended to embrace all structural isomeric forms of paraffins. The term "acyclic paraffin" refers to straight-chain or branched-chain paraffins. The term "isoparaffin" refers to branched-chain paraffins and the term "n-paraffin" or "normal paraffin" refers to straight-chain paraffins.

As used herein, and unless otherwise specified, the term "naphthene" refers to a cycloalkane (also known as a cycloparaffin) having from 3-80 carbon atoms. Examples of naphthenes include, but are not limited to cyclopropane, cyclobutane, cyclopentane, cyclohexane, cycloheptane, cyclooctane and the like. The term naphthene encompasses single-ring naphthenes and multi-ring naphthenes. The multi-ring naphthenes may have two or more rings, e.g., two-rings, three-rings, four-rings, five-rings, six-rings, seven-rings, eight-rings, nine-rings, and ten-rings. The rings may be fused and/or bridged. The naphthene can also include various side chains, particularly one or more alkyl side chains of 1-30 carbons.

In some aspects, a hydrocarbon sample analyzed using the methods described herein may include a sample of a "vacuum gas oil" (VGO), a "vacuum residue" (VR), refined petroleum intermediate streams/products or a combination thereof. According to at least some conventional definitions, "VGO" is a crude oil fraction that boils between about 343° C. (about 650° F.) to 538° C. (about 1000° F.), and "VR" is a residue obtained by vacuum distillation of a crude oil and boils above a temperature about 538° C.

Some petroleum streams, such as wax, certain lubricant base oil, base stocks, and bright stocks, contain at least 90% of petroleum saturate compounds. These materials may contain trace amounts of olefins, or from 0 wt % to about 1 wt % of olefin compounds, that can be detected and analyzed by the methods described herein without additional preparation or separation steps.

In particular, "base stocks" may be used for the production of lubricants, such as lubricating oils for automotives, industrial lubricants and lubricating greases. A "base oil" is defined as a combination of two or more base stocks used to make a lubricant composition. Base stocks may also be used as process oils, white oils, metal working oils and heat transfer fluids. Finished lubricants consist of two general components, lubricating base stock and additives. Lubricating base stock is the major constituent in these finished lubricants and contributes significantly to the properties of the finished lubricant. In general, a few lubricating base stocks are used to manufacture a wide variety of finished lubricants by varying the mixtures of individual lubricating base stocks and individual additives.

Base stocks may be categorized based on their saturated hydrocarbon content, sulfur level, and viscosity index. Lubricant base stocks are typically produced in large scale from non-renewable petroleum sources. Some base stocks may be derived from crude oil via extensive processing, such as solvent extraction, solvent or catalytic dewaxing, and hydroisomerization. Other base stocks may be produced from synthetic hydrocarbon liquids obtained from natural gas, coal or other fossil resources. Other base stocks, the polyalphaolefins (PAO), may be produced by oligomerization of alpha olefins, such as 1-decene. Other base stocks may include naphthenics, polyalkylene glycols (PAG), and esters.

The hydrocarbon samples of the methods described herein may include samples of base stocks, bright stocks, lubricant base oils, vacuum gas oils, vacuum residues, petroleum streams, combinations thereof, fractions thereof, concentrates thereof, extracts thereof, dilutes thereof, components thereof, and mixtures containing the same.

The hydrocarbon samples of the methods described herein may contain at least about 90 wt % of saturate compounds, or at least 95 wt % of saturate compounds, of at least 99 wt % of saturate compounds. Further, hydrocarbon samples of the methods described herein may contain about 0.01 wt % or more of olefin compounds, or from about 0.05 wt % to about 90 wt % of olefin compounds, or from about 0.1 wt % to about 50 wt % of olefin compounds, or from about 0.1 wt % to about 10 wt % of olefin compounds, or from about 0.1 wt % to about 1 wt % of olefin compounds.

The hydrocarbon samples of the methods described herein may have a viscosity of about 1 to about 100 cSt at 100° C., of about 2 to about 50 cSt at 100° C., or of about 3 to about 50 cSt at 100° C. The hydrocarbon samples of the methods described herein may have a viscosity index of about 90 or greater, or of about 100 to about 200.

The hydrocarbon sample may include a heavy hydrocarbon sample. The heavy hydrocarbon sample may have a boiling point of at least about 300° C., of at least about 320° C., of at least about 340° C., of at least about 350° C., of at least about 375° C., of at least about 400° C., of at least about 450° C., of at least about 500° C., or of at least about 550° C. The boiling point profile for a heavy hydrocarbon can be determined by a suitable ASTM distillation method, such as ASTM D86.

The petroleum saturate compounds may include heavy hydrocarbons. The heavy hydrocarbons may have boiling points of at least about 300° C., of at least about 320° C., of at least about 340° C., of at least about 350° C., of at least about 375° C., of at least about 400° C., of at least about 450° C., of at least about 500° C., or of at least about 550° C.

The hydrocarbon sample may be such that about 10 wt % or less of the hydrocarbons in the sample have a molecular weight of 300 Daltons or less, or such that about 5 wt % or less of the hydrocarbons in the sample have a molecular weight of 400 Daltons or less.

The methods for selective detection and analysis of olefins in high boiling petroleum fractions may use ESI-MS. The method may include the preparation of a solution comprising a hydrocarbon sample and an effective amount of an ionization agent, or a metal salt comprising a metal ion, and the formation of olefin-metal ion complex by electrospray ionization, such complex being then detected using MS. The method may further comprise obtaining a mass spectrum of the olefin-metal ion complexes obtained from ESI of the mixture of hydrocarbon sample and metal ion, and assigning molecular formula to the olefin-metal ion complexes in the mass spectrum.

The method and ionization agents described herein provide substantially improved detection and analysis of olefins among the mixture of compounds in a hydrocarbon sample from base stocks, bright stocks, lubricant base oils, vacuum gas oils, vacuum residues, petroleum streams, combinations thereof, fractions thereof, concentrates thereof, extracts thereof, dilutes thereof, components thereof, and mixtures containing the same.

Analysis of the hydrocarbon sample may include analyzing the solution comprising an olefin-metal ion complex with an electrospray ionization mass spectrometer. The electrospray ionization mass spectrometer can be an electrospray ionization Fourier-transform ion cyclotron resonance mass spectrometer (ESI FT-ICR MS).

The amount of the ionization reagent or metal salt, e.g., silver nitrate, added to the solution of hydrocarbon can be an effective amount. As used herein, an "effective amount" is an amount sufficient to produce complexation of the olefin and metal cation that is detectable via mass spectroscopy.

Although the exact amount of the ionization reagents or metal salts can vary depending on the specific hydrocarbon sample, the metal salt may be added to the hydrocarbon sample in solutions having a concentration of about 1 ppm or more. Further, the mass ratio of olefin contained in the hydrocarbon sample composition to the metal salt may be 100:1 to 1:100, or 10:1 to 1:10, or 5:1 to 1:7, or 4:1 to 1:5.

The method can include a reaction of the ionization agents with the olefins in the hydrocarbon sample for a sufficient time to convert a portion of the olefins into ionic target species. As the ionization reagent, silver nitrate, may be reactive even during direct capillary mixing just prior to ionization in the ESI.

In ESI, a metal salt such as silver nitrate may be used as an ionization reagent that has a strong ability to bind to a source of electrons, e.g., electrons in $\pi$ orbitals, and offers a rapid method that generates positively charged complexes of metal ions with olefin molecules present in the oil components. As such, the use of metal salts enables enhanced identification of olefin species in complex mixtures containing hydrocarbons, such as base stocks, bright stocks, lubricant base oils, vacuum gas oils, vacuum residues, petroleum streams, combinations thereof, fractions thereof, concentrates thereof, extracts thereof, dilutes thereof, components thereof, and mixtures containing the same.

Silver ions ($Ag^+$) are an example of a suitable metal cation that can form an ion complex or adduct with the double bond of an olefin. Instead of ionizing the olefin, an olefin and silver ion adduct can be formed, so that the silver ion accommodates the ionic charge. This results in a substantially lower fragmentation rate for the olefinic compounds as compared to forcing the olefinic compounds to directly carry the ionic charge (such as in high energy electron impact ionization). It is believed that other metal cations or Lewis acids may serve the same purpose as silver cations. Other examples of suitable metal cations or Lewis acids include noble metal ions, as well as transition metal ions. Examples of suitable metal cations in a "+1" oxidation state include $Ag^+$, $Au^+$, $Cu^+$, $Tl^+$, $Hg^+$, and $Cs^+$. Examples of suitable metal cations in a "+2" oxidation state include $Pt^{2+}$, $Pd^{2+}$, $Cd^{2+}$, $Pr^{2+}$, and $Hg^{2+}$.

The counter-anions of the metal salts may include any suitable anion, for example nitrate, acetate, trifluoromethanesulfonate, sulfate, fluorosulfate, chloride, iodide, hydroxide, tetrafluoroborate, carbonate, bicarbonate, phosphate, carbamate, formate, gluconate, acorbate, benzoate, citrate, perchlorate, nitrite, heptafluorobutyrate, hexafluorophosphate, or perfluorobutanesulfonate.

Additionally, the characteristic isotope signature of silver ($^{107}Ag$ and $^{109}Ag$, differing by 1.9997 Da) may be used to differentiate between olefins and other types of ions that may form through another mechanism. For example, a protonated ion will not have the characteristic isotope signature, and that data can be filtered.

In addition, FT-ICR MS may be used for mass analysis and compositional analysis of the samples according to the methods described herein. The FT-ICR MS conditions may be fine-tuned for the molecular mass range of interest. In the examples provided herein, data are typically collected in a broadband acquisition mode (a mass range of 100 Da to 3000 Da). Preferably, Fourier-transform ion cyclotron resonance mass spectrometry (FT-ICR MS) with an average mass resolving power (RP>1M) is utilized for the analysis. FT-ICR MS allows for resolution and determination of masses with high accuracy (error <0.2 ppm). Concentrations of the masses were estimated by the signal magnitude of corresponding masses. Empirical formulas can be determined without ambiguity within the accuracy of mass analysis window and restrictions of heteroatom combinations. Chromatographic separation may be used to form a saturates portion for analysis by separating saturates from other compounds in a petroleum sample. Molecular structure assignments are made based on empirical formulas. Thus, composition may be reconciled so that average composition and properties are consistent with other optional measured properties by bulk measurement technologies, such as NMR and elemental analysis.

In FT-ICR MS, the excited cyclotron motion of the ions is detected on receiver plates as a time domain signal that contains all the cyclotron frequencies that have been excited. Fourier transformation of the time domain signal results in the frequency domain signal that can be converted into a mass spectrum. In the methods described herein, the mass range was set at m/z 100 to 3000, and the dataset size was set to 8 Megawords. Ion accumulation time was 10 to 55 msec. 100, 200, or 300 data sets were co-added to generate the final spectrum. Bruker Data Analysis (DA) software is used to find the mass peak list with signal-to-noise ratio (S/N) greater than 6. The mass peak list is further analyzed for identification of hydrocarbon molecules. External mass calibration was performed using commercial Agilent ESI Tuning Mix (Agilent Part No. G2431A). In general, <0.2 ppm mass accuracy can be achieved with external calibration.

FT-ICR MS may provide chemical information for a hydrocarbon sample by assigning Z-numbers, such that the more negative the Z-number, the more unsaturated the molecules. In general, for hydrocarbon molecules, z=2 corresponds to alkanes, z=0 corresponds to olefins and 1 ring cycloalkanes, z=−2 to −4 corresponds to multi-ring cycloalkanes, and z=−6 or less corresponds to aromatics, cycloalkyl aromatics, and multi-ring aromatics.

Preferably, the molecular formula of detected compounds are assigned for mass peaks having greater than a threshold level of signal-to-noise ratio using a mass tolerance of 0.6 mDa. Preferably, the assignments are made by assuming that only C, H, and Ag atoms are present in the detected ions. During assignment of the molecular formula, the number of certain types of atoms, such as Ag, can be limited to a maximum number per atom. For example, the maximum number of Ag atoms can be limited to 1.

As such, when coupled to FT-ICR MS, the methods described herein may yield molecular level compositional data on the olefins of various samples of base stocks, bright stocks, lubricant base oils, vacuum gas oils, vacuum residues, petroleum streams, combinations thereof, fractions thereof, concentrates thereof, extracts thereof, dilutes thereof, components thereof, and mixtures containing the same.

EXAMPLE EMBODIMENTS

Embodiments disclosed herein include

A. A method comprising: obtaining a hydrocarbon sample comprising at least about 90 wt % of saturate compounds; producing a solution comprising the hydrocarbon sample and a metal salt, the metal salt comprising a metal ion; forming olefin-metal ion complexes by electrospray ionization (ESI); and detecting the olefin-metal ion complexes using mass spectrometry (MS).

Embodiment A may have one or more of the following additional elements in any combination:

Element 1: wherein the hydrocarbon sample comprises 0.01 wt % or more of olefin compounds having one or more double bonds.

Element 2: further comprising obtaining a mass spectrum of the olefin-metal ion complexes; and assigning molecular formula to the olefin-metal ion complexes in the mass spectrum.

Element 3: wherein the olefin-metal ion complexes are detected using Fourier-transform ion cyclotron resonance (FT-ICR) mass spectrometry.

Element 4: wherein the metal ion is selected from the group consisting of $Ag^+$, $Au^+$, $Cu^+$, $Tl^+$, $Hg^+$, $Cs^+$, $Pt^{2+}$, $Pd^{2+}$, $Cd^{2+}$, $Pr^{2+}$, and $Hg^{2+}$.'

Element 5: wherein the metal ion is $Ag^+$.

Element 6: wherein the metal salt is a silver salt.

Element 7: wherein the metal salt is a silver nitrate, silver acetate, silver trifluoromethanesulfonate, silver sulfate, silver fluorosulfate, silver chloride, silver iodide, silver hydroxide, silver tetrafluoroborate, silver carbonate, silver bicarbonate, silver phosphate, silver carbamate, silver formate, silver gluconate, silver acorbate, silver benzoate, silver citrate, silver perchlorate, silver nitrite, silver heptafluorobutyrate, silver hexafluorophosphate, or silver perfluorobutanesulfonate.

Element 8: wherein the hydrocarbon sample has a viscosity of 1 to 100 cSt at 100° C.

Element 9: wherein the hydrocarbon sample has a viscosity of 2 to 50 cSt at 100° C.

Element 10: wherein the hydrocarbon sample comprises from 10 to 99 wt % paraffins.

Element 11: wherein the hydrocarbon sample comprises from 15 to 30 wt % paraffins.

Element 12: wherein the hydrocarbon sample comprises from 20 to 90 wt % of a mixture of naphthenes and aromatics.

Element 13: wherein the hydrocarbon sample comprises from 35 to 65 wt % a mixture of naphthenes and aromatics.

Element 14: wherein the hydrocarbon sample has a boiling temperature of at least 300° C.

Element 15: wherein the hydrocarbon sample has a boiling temperature of at least 340° C.

By way of non-limiting example, exemplary combinations applicable to A include, but are not limited to, Element 1 in combination with one or more of Elements 2-15; Element 1 in combination with one or more of Elements 2 and 3 and two or more of Elements 4-15; Element 1 in combination with Element 2 and one or more of Elements 3-11. Element 1 in combination with Element 2 and two or more of Elements 3-11. Element 1 in combination with Element 2 and one or more of Elements 12-15. Element 1 in combination with Element 2 and two or more of Elements 12-15.

To facilitate a better understanding of the embodiments described herein, the following examples of various representative embodiments are given. In no way should the following examples be read to limit, or to define, the scope of the invention.

EXAMPLES

Based on the above, ESI-MS may be used to analyze and detect olefins in a petroleum sample. The examples below were performed on either a Waters Synapt G2 S time of flight mass spectrometer or a Bruker 15T Solarix XR FT-ICR mass spectrometer. The compositions of the examples were prepared by dissolving a sample of a hydrocarbon mixture in a non-aromatic, non-olefinic solvent or mixture of non-aromatic, non-olefinic solvents based on the sample's solubility (e.g., acetonitrile, methanol, hexane, etc.) and adding a small (1-200 ppm) amount of silver nitrate dissolved in isopropanol or other solvent that can both solubilize silver nitrate and be miscible in the sample solvent at the concentration used.

Example 1: Model Compounds Study

Figure 1D:
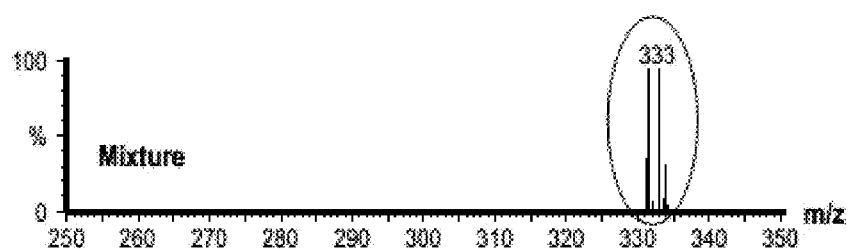

Paraffin standards were diluted to 20 ppm (v/v) in toluene/methanol, 7:3. Olefin standards were tested individually, and also as an equal molar solution (0.05 mM), and were dissolved in 2-propanol:hexane, 1:1. A concentrated stock solution of silver nitrate was prepared in acetonitrile, at 2,000 ppm (w/v). Silver nitrate solution was added to between 1 and 100 ppm (v/v) from the concentrated stock. FIGS. 1A-D show the MS spectra obtained from an instrument blank (FIG. 1A), 1-hexadecene (olefin) (FIG. 1B), cyclohexylhexane (naphthene) (FIG. 1C), and a mixture of 1-hexadecene and cyclohexylhexane (FIG. 1D). As can be seen on the spectra, only the olefin 1-hexadecene is observable on the spectra of FIGS. 1B and 1D at m/z 331 and 333, respectively, as this olefin is the only compound having a charge through complexation with silver cation upon on ESI. Further, the complex has the characteristic isotope signature showing two peaks with a difference of 2 Da and having nearly equal intensity. Experiments conducted with paraffinic molecules similarly yielded no signal.

Example 2: Detection of Olefin Model Compounds in VGO Saturates Fractions

Figure 2:
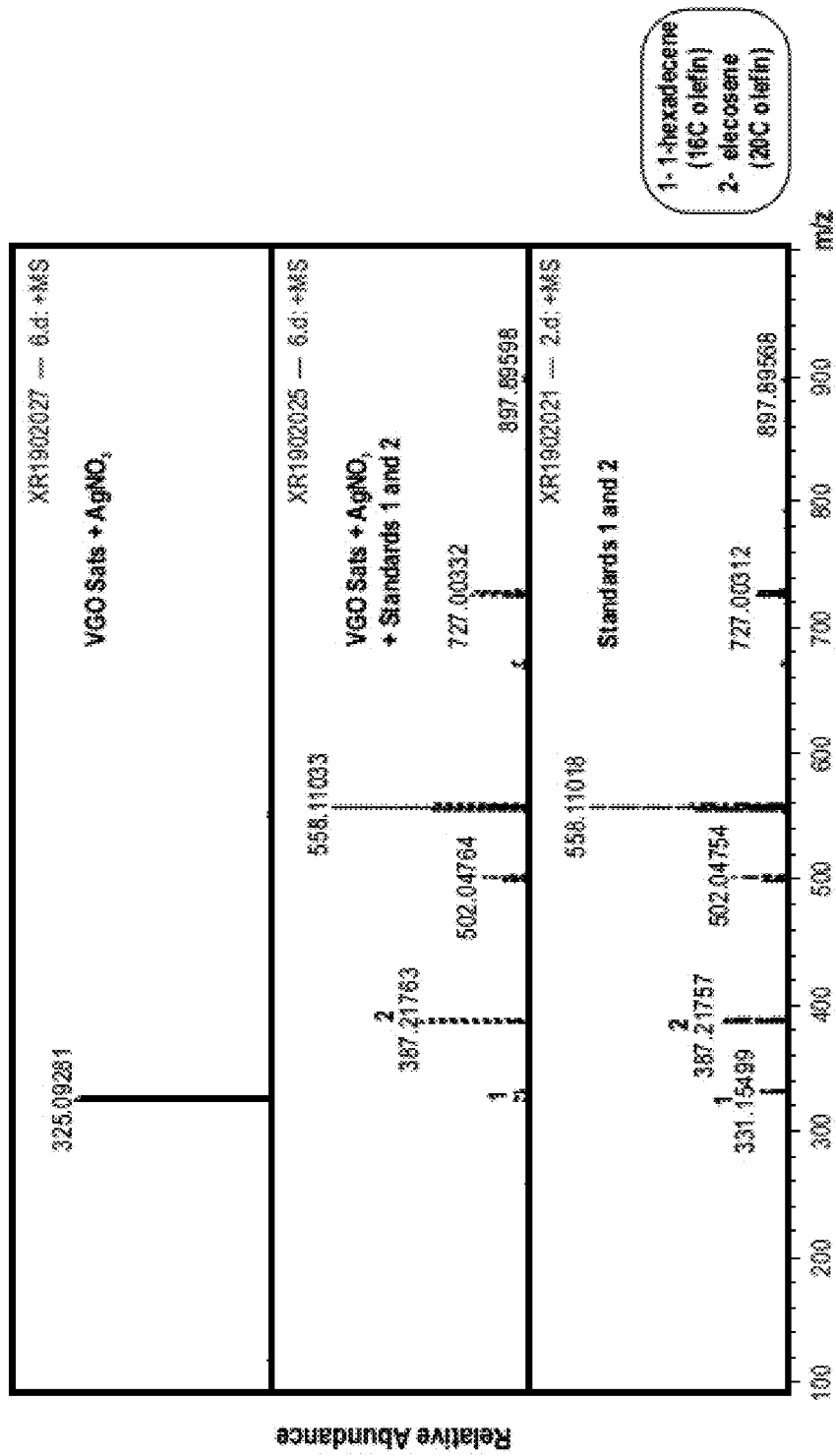
FIG. 2 illustrates the detection of olefins model compounds (C16 and C20 olefins) in a saturates fraction of a vacuum gas oil (VGO) obtained in Example 2.

The saturates VGO fraction was diluted to between 100 and 1000 ppm (w/v) in toluene/methanol (7:3 by volume), toluene/methanol (1:1 by volume), and 2-propanol/hexane (1:1 by volume). A concentrated stock solution of silver nitrate was prepared in acetonitrile, at 2,000 ppm (w/v). Silver nitrate solution was added to between 1 and 100 ppm (v/v) from the concentrated stock. FIG. 2 shows an example of the detection of olefins added in a saturates fraction of the vacuum gas oil (VGO). In this example, the MS spectra of a sample of VGO and silver nitrate (top spectrum); of a sample comprising VGO, silver nitrate, and two olefins standards (1-hexadecene and eicosene) (middle spectrum); and of a sample comprising the two olefin standards (bottom spectrum), show only one noise peak observed in the VGO saturates fraction at m/z 325 (top spectrum), and only peaks from the standard mixture (bottom spectrum) appear when added in the VGO saturates composition (middle spectrum).

Example 3: Detection of Olefin Model Compounds in VR Saturates Fraction

Figure 3:
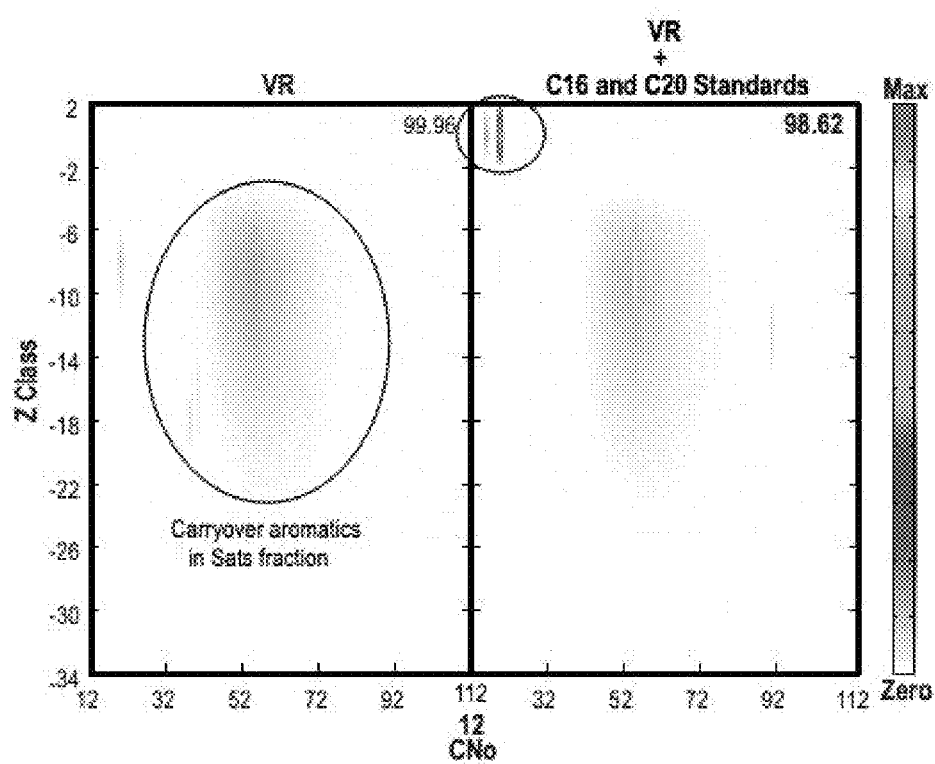
FIG. 3 shows the detection of olefins model compounds (C16 and C20 olefins) in a saturates fraction of a vacuum residue (VR) obtained in Example 3.

The saturates VR fraction was diluted to between 100 and 1000 ppm (w/v) in toluene/methanol (7:3 by volume), toluene/methanol (1:1 by volume), and 2-propanol/hexane (1:1 by volume). A concentrated stock solution of silver nitrate was prepared in acetonitrile, at 2,000 ppm (w/v). Silver nitrate solution was added to between 1 and 100 ppm (v/v) from the concentrated stock. FIG. 3 shows the molecular composition distribution of the saturates fraction of the vacuum residue (VR) using the method described herein. The hydrocarbon molecules are separated into Z classes. Z is a measure of hydrogen deficiency and is calculated for hydrocarbons by using the general chemical formula $C_cH_{2c+z}$. As shown on FIG. 3, only trace aromatics ($Z \leq -6$) are detected and are likely carryover 1-ring aromatics due to an imperfect separation. Benzenes, indanes and indenes have Z numbers of $-6$, $-8$ and $-10$, respectively (left oval). After adding in the two olefin standards (right oval), hexadecene and eicosene, the signal for these ions dominates the spectrum ($Z>2$).

Example 4: Detection of Trace Level of Olefins in Lubricant Base Stocks

Figure 4:
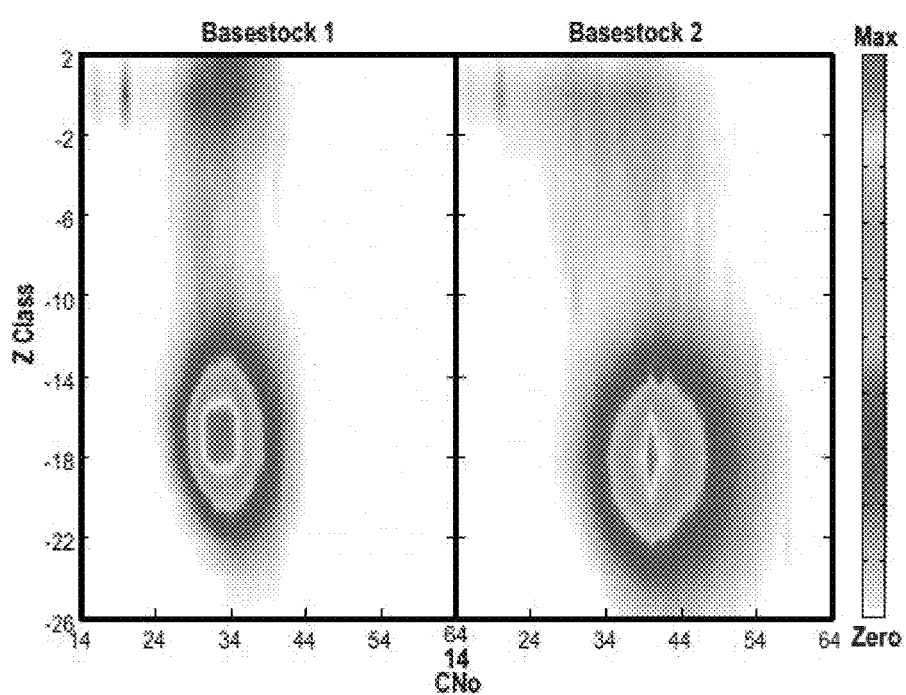
FIG. 4 shows the molecular composition distributions of trace olefins in a light lubricant base stock and a heavy lubricant base stock obtained in Example 4.

Two commercial Group II base stocks of different carbon number ranges were diluted to 1000 ppm in 2-propanol:hexane, 1:1. While it was known that Group II base stocks have some aromatics content, it was previously unknown if trace levels of olefins were also present. Using this method, a small amount of olefins were observed at $Z=0$, $-2$ and $-4$ as shown in FIG. 4 for both base stocks. Similar to the VR and VGO above, the spiked standards are readily visible when added. As such paraffins, which were not previously observed in the model compound, VR, or VGO samples, contribute a small amount of signal for these samples.

Example 5: Quantitation.

Quantitation may be achieved by the standard addition method by adding olefin model compounds in known amounts into blank saturate samples and comparing the mass spectrum of an unknown sample with those of the model compounds in order to estimate the unknown amounts of olefin. As such, quantitative data may be obtained for olefins of various samples on the olefins of various samples of base stocks, bright stocks, lubricant base oils, vacuum gas oils, vacuum residues, petroleum streams, combinations thereof, fractions thereof, concentrates thereof, extracts thereof, dilutes thereof, components thereof, and mixtures containing the same.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa. The term "and/or" as used in a phrase such as "A and/or B" herein is intended to include "A and B," "A or B," "A," and "B." Numerical ranges used herein include the numbers recited in the range. For example, the numerical range "from 1 wt % to 10 wt %" includes 1 wt % and 10 wt % within the recited range.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

One or more illustrative incarnations incorporating one or more invention elements are presented herein. Not all features of a physical implementation are described or shown in this application for the sake of clarity. It is understood that in the development of a physical embodiment incorporating one or more elements of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

Therefore, the present invention is well adapted to attain the ends and advantages mentioned as well as those that are inherent therein. The particular examples and configurations disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative examples disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method comprising:
   obtaining a hydrocarbon sample comprising at least about 90 wt % of saturate compounds, wherein the hydrocarbon sample has a viscosity of 1 to 100 cSt at 100° C., in order to detect low olefin content in high-viscosity hydrocarbon samples;
   producing a solution comprising the hydrocarbon sample and a metal salt, the metal salt comprising a metal ion;
   forming olefin-metal ion complexes by positive ion electrospray ionization (ESI); and
   detecting the olefin-metal ion complexes using mass spectrometry (MS).

2. The method of claim 1, wherein the hydrocarbon sample comprises 0.01 wt % or more of olefin compounds having one or more double bonds.

3. The method of claim 1, further comprising:
   obtaining a mass spectrum of the olefin-metal ion complexes; and
   assigning molecular formula to the olefin-metal ion complexes in the mass spectrum.

4. The method of claim 1, wherein the olefin-metal ion complexes are detected using Fourier-transform ion cyclotron resonance (FT-ICR) mass spectrometry.

5. The method of claim 1, wherein the metal ion is selected from the group consisting of Ag+, Au+, Cu+, Tl+, Hg+, Cs+, $Pt^2+$, $Pd^2+$, $Cd^2+$, $Pr^2+$, and $Hg^2+$.

6. The method of claim 5, wherein the metal ion is Ag+.

7. The method of claim 1, wherein the metal salt is a silver salt.

8. The method of claim 7, wherein the metal salt is a silver nitrate, silver acetate, silver trifluoromethanesulfonate, silver sulfate, silver fluorosulfate, silver chloride, silver iodide, silver hydroxide, silver tetrafluoroborate, silver carbonate, silver bicarbonate, silver phosphate, silver carbamate, silver formate, silver gluconate, silver acorbate, silver benzoate, silver citrate, silver perchlorate, silver nitrite, silver heptafluorobutyrate, silver hexafluorophosphate, or silver perfluorobutanesulfonate.

9. The method of claim 1, wherein the hydrocarbon sample has a viscosity of 2 to 50 cSt at 100° C.

10. The method of claim 1, wherein the hydrocarbon sample comprises from 10 to 99 wt % paraffins.

11. The method of claim 10, wherein the hydrocarbon sample comprises from 15 to 30 wt % paraffins.

12. The method of claim 1, wherein the hydrocarbon sample comprises from 20 to 90 wt % of a mixture of naphthenes and aromatics.

13. The method of claim 12, wherein the hydrocarbon sample comprises from 35 to 65 wt % a mixture of naphthenes and aromatics.

14. The method of claim 1, wherein the hydrocarbon sample has a boiling temperature of at least 300° C.

15. The method of claim 14, wherein the hydrocarbon sample has a boiling temperature of at least 340° C.

16. The method of claim 1, wherein the hydrocarbon sample is selected from the group consisting of a base stock, a bright stock, a lubricant base oil, a vacuum gas oil, a vacuum residue, a fraction thereof, a concentrate thereof, an extract thereof, a dilute thereof, a component thereof, and any combination thereof.

17. The method of claim 1, wherein the hydrocarbon sample is selected from the group consisting of a base stock, a bright stock, and any combination thereof; and wherein the hydrocarbon sample is produced from solvent extraction of vacuum residue.

18. The method of claim 1, wherein the hydrocarbon sample comprises 10% or less of hydrocarbons having a molecular weight of 300 Daltons or less.

19. A method comprising:
obtaining a hydrocarbon sample comprising at least about 90 wt % of saturate compounds,
wherein the hydrocarbon sample has a viscosity of 1 to 100 cSt at 100° C., in order to detect low olefin content in high-viscosity hydrocarbon samples,
wherein the hydrocarbon sample is selected from the group consisting of a base stock, a bright stock, and any combination thereof, and
wherein the hydrocarbon sample is produced from solvent extraction of vacuum residue;
producing a solution comprising the hydrocarbon sample and a metal salt, the metal salt comprising a metal ion;
forming olefin-metal ion complexes by positive ion electrospray ionization (ESI); and
detecting the olefin-metal ion complexes using mass spectrometry (MS).

20. The method of claim 19, wherein the hydrocarbon sample comprises 10% or less of hydrocarbons having a molecular weight of 300 Daltons or less.

* * * * *